US008337776B1

(12) United States Patent
D'Onofrio et al.

(10) Patent No.: US 8,337,776 B1
(45) Date of Patent: Dec. 25, 2012

(54) CLOSED-LOOP WASTE DISPOSAL SYSTEM FOR ENHANCED SAFETY

(75) Inventors: Terrence G. D'Onofrio, Bel Air, MD (US); George Noya, Bel Air, MD (US); Luis Enrique Faure, Abingdon, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/443,293

(22) Filed: Apr. 10, 2012

(51) Int. Cl.
*A61L 9/00* (2006.01)
*G01N 37/00* (2006.01)
(52) U.S. Cl. ........ 422/500; 422/297; 422/300; 422/567; 435/288.5
(58) Field of Classification Search .................... 422/500
See application file for complete search history.

(56) References Cited

U.S. PATENT DOCUMENTS

| | | | | | |
|---|---|---|---|---|---|
| 3,922,974 | A | * | 12/1975 | Hempelmann | 110/237 |
| 3,986,835 | A | * | 10/1976 | Takagi | 422/71 |
| 2001/0004060 | A1 | * | 6/2001 | Chilibeck | 210/137 |
| 2003/0136716 | A1 | * | 7/2003 | Moffitt et al. | 210/121 |
| 2006/0130752 | A1 | * | 6/2006 | McLaughlin | 118/313 |
| 2009/0076470 | A1 | * | 3/2009 | Ryan | 604/319 |

FOREIGN PATENT DOCUMENTS

GB 2030503 A * 4/1980

* cited by examiner

*Primary Examiner* — Jill Warden
*Assistant Examiner* — Brittany Fisher
(74) *Attorney, Agent, or Firm* — Ulysses John Biffoni

(57) ABSTRACT

A system and method to safely dispose of hazardous liquid waste includes a glove box for conducting a test with a hazardous liquid material therein, the glove box having a drainage line connected to a waste tank for directing the hazardous liquid waste from the glove box to the waste tank. A waste disposal line and an air vent line are connected between the waste tank and a waste container. Double-valved connectors are positioned in the waste disposal line and in the air vent line allowing the liquid waste and air to flow between the waste tank and a waste container when the double-valved connectors are coupled together. When the double-valved connectors are uncoupled, both the waste tank and the waste container are completely sealed to the surrounding environment.

20 Claims, 4 Drawing Sheets

CLOSED-LOOP WASTE DISPOSAL SYSTEM FOR ENHANCED SAFETY

GOVERNMENT INTEREST

The invention described herein may be manufactured, used, and licensed by or for the United States Government.

TECHNICAL FIELD OF THE INVENTION

The present invention relates generally to a waste disposal system for enhanced safety. More specifically, the present invention relates to a dosed loop waste disposal system wherein hazardous waste, generally a liquid, is contained at all times, with no need for any open container while outside the engineering controls, so there is a decreased risk of spillage and/or off-gassing of dangerous and hazardous materials.

BACKGROUND OF THE INVENTION

Small environment isolation chambers or, as they are more commonly called, glove boxes, are extensively used in research, industry and medicine to facilitate the hand manipulation of an object of one sort or another within an isolated environment. To enable manipulation of the object within the chamber, rubber gloves are normally provided projecting into the chamber enclosure with their sleeve ends sealed around an opening through a wall of such enclosure. The gloves provide, in effect, a continuation of the chamber enclosure wall and separate not only an operator's hands extended through the opening from the interior of the enclosure, but also keep the ambient atmosphere and glove box air segregated. The chemicals handled within a glove box are often hazardous. This invention increases the operational safety of the glove box by reducing the potential for exposure during waste handling.

SUMMARY OF THE INVENTION

According to an embodiment of the present invention, a system is provided to safely dispose of hazardous liquid waste. The system includes a glove box for conducting a test with a hazardous liquid material therein, the glove box having a drainage line connected to a waste tank for directing the hazardous liquid waste from the glove box to the waste tank. A waste disposal line connects at one end to the waste tank and at the second end to a waste container. There is a double-valved connector connected at one end to the waste disposal line and at the opposite end to the waste container, the double-valved connector including a coupling insert secured at one end to the waste container and having a first biased valve closing the opposite open end thereof, the double-valved connector having a coupling body secured at one end to the waste disposal line and having a second biased valve closing the opposite opened end thereof, and the coupling insert being removably secured to the coupling body. When the coupling insert is secured to the coupling body, the first and second biased valves are open so that liquid waste can flow from the waste tank to the waste container. When the coupling body is uncoupled from the coupling insert, the first and second biased valves in the coupling insert and the coupling body are biased closed such that both the waste tank and the waste container are completely sealed to the surrounding environment.

According to another embodiment of the present invention, a method is provided for safely disposing of hazardous liquid waste. The method includes conducting a test with a hazardous liquid material in a glove box and directing the hazardous liquid waste from the glove box to a waste tank through a drainage line. The method further includes connecting the waste tank to a waste container with a waste disposal line, and then connecting the waste disposal line to the waste container with a double-valved connector having a coupling insert connected at one end to the waste container and with a first biased valve closing an opposite end thereof and a coupling body with a second biased valve closing one end and connected at an opposite end of the waste disposal line. Then, removably securing the coupling insert being to the coupling body whereby when the first and second biased valves are open liquid waste can flow from the waste tank to the waste container. Finally, uncoupling the coupling body from the coupling insert whereby the first and second biased valves are biased closed so that both the waste tank and the waste container are completely sealed to the surrounding environment.

BRIEF DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

DETAILED DESCRIPTION OF THE PREFERRED EMBODIMENTS

Figure 1:
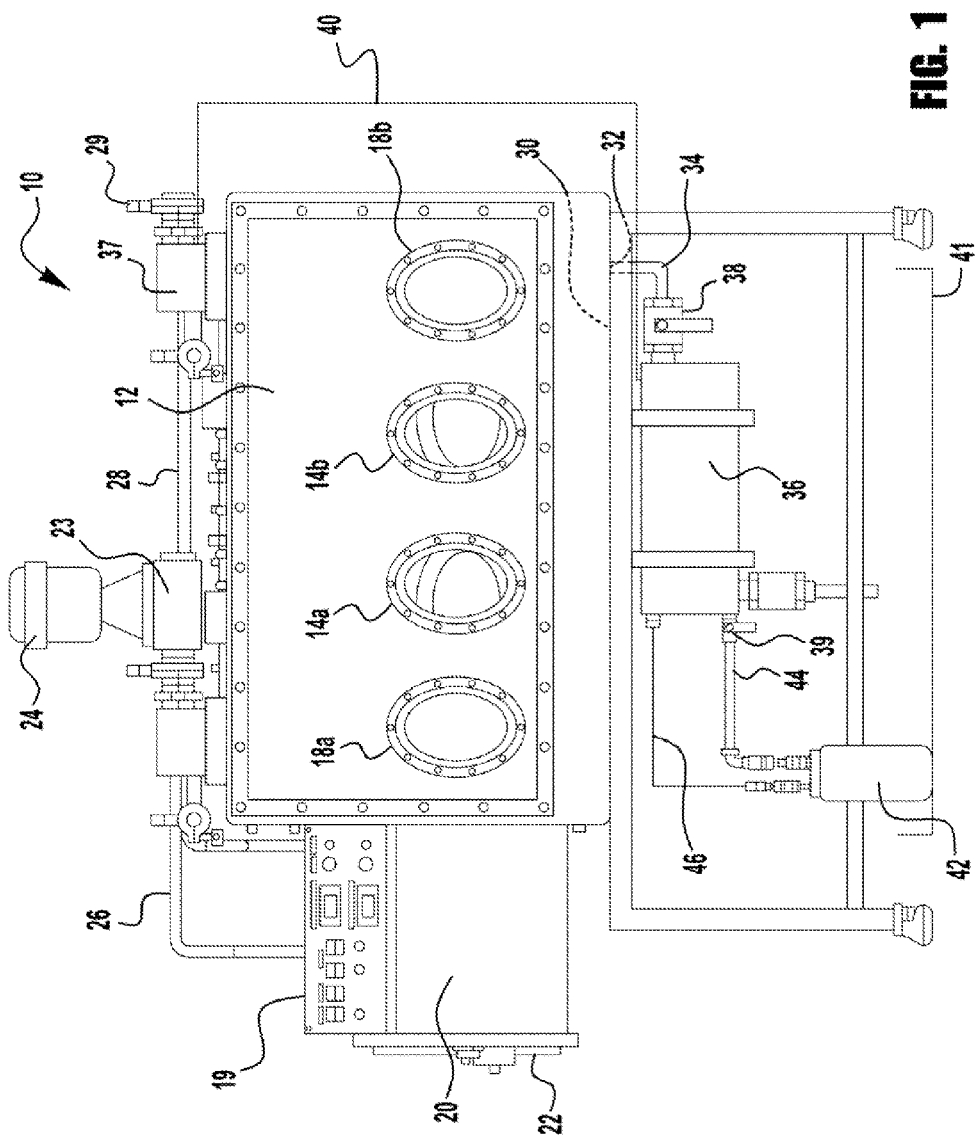
FIG. 1 is a front view of a waste disposal system for enhanced safety, in accordance with the present invention.

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

The present invention is directed to a waste disposal system 10 for enhanced safety (hereafter "disposal system"), as shown in FIG. 1. The disposal system 10 is used as a closed loop system for hazardous waste disposal. One aspect of this system is that hazardous waste, generally a liquid, is contained at all times, with no need for any open container while outside the engineering controls (glove box, fume hood, etc. as described below). This closed loop system 10 enhances safety so there is a decreased risk of spillage and/or off-gassing of dangerous and hazardous materials. Because the disposal system 10 remains closed, there is an increased level of safety to the operators.

Figure 2:
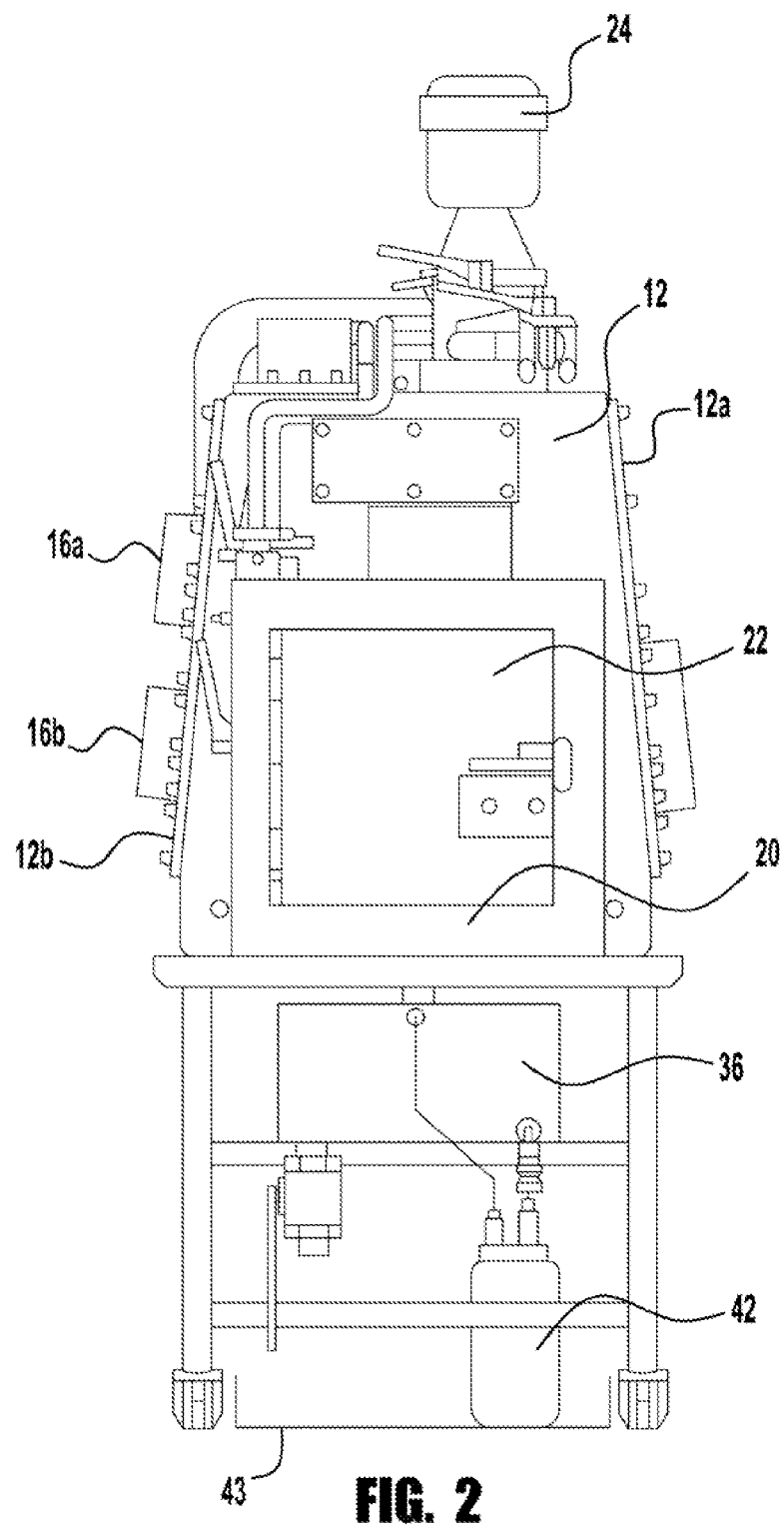
FIG. 2 is a side view of a waste disposal system for enhanced safety, in accordance with the present invention.

FIGS. 1 and 2 illustrate the disposal system 10, containing a variety of engineering controls for conducting chemical tests. The chemical tests are performed within glove box 12, which provides the primary engineering control and primary protection during a hazardous test operation. Glove box 12 is a sealed container that is designed to allow one to manipulate objects where a separate atmosphere is desired. A typical glove box is constructed of a 316 stainless steel body and polycarbonate windows. Also, a typical glove box can be constructed to have glove ports on one or two sides. In this case, there are glove ports on both sides of the glove box 12. Built into the sides 12*a* and 12*b* of the glove box 12 are openings 14*a* and 14*b* through side 12*a* and openings 16*a* and 16*b* through side 12*b*. The glove ports are mounted on a polycarbonate window (or other clear material); the window allowing the user to see what is being manipulated. The glove ports designated by reference numerals 14*a*, 14*b*, 16*a*, 16*b*, 18*a*, and 18*b* are glove ports located on the window to allow the operator to manipulate the sample. Although not shown on the drawings, there are four glove ports on each side of the glove box.

Glove box 12 includes a control panel 19, an airlock 20 with interlocked doors 22 to introduce items into the glove box 12 or remove items from the glove box 12. Airlock 20 is attached to glove box 12. Attached to the air inlet valve 23 is a biased-closed pneumatic actuator 24, which can be opened by applying compressed air. Opening the actuated valve allows room air to enter the glove box 12 and out of an exhaust outlet 29, where it is then directed to an external filtration system which exhausts the filtered air out. Pneumatic actuator 24 only opens for incoming air. This prevents "contaminated" air from the glove box from leaving through the input valve to the open air. In the event of an alarm, indicating insufficient pressure in the glove box, the actuated valve automatically closes.

At the end of a chemical test, there may be liquid present at the bottom, interior surface 30 of the glove box 12, especially after a decontamination procedure. The bottom, interior surface 30 of the glove box 12 is sloped towards a drain 32 to facilitate cleanup. There is a drainage line 34, which directs the hazardous liquid waste from the glove box 12 to a waste tank 36. Waste tank 36 is the permanent and primary hazardous waste storage unit. A typical waste tank 36 used is 15 gallons and constructed of polypropylene. During normal operation of chemical tests, waste tank 36 stores the hazardous liquid waste produced in glove box 12. There is a lockable valve 38, such as a drain ball valve, between the glove box 12 and the waste tank 36, so that the liquid does not drain from the glove box to the waste tank until the user chooses to do so and unlocks the valve. There is also an air vent line 40 between waste tank 36 and the exhaust plenum 37 to allow the trapped air from the waste tank and the waste container (described below) 42 to exhaust out through the exhaust plenum 37 of the glove box 12, and ultimately through the exhaust outlet 29 (as described above). There is also a lockable valve 39, such as a drain ball valve, between the waste tank 36 and the waste disposal line 44, to be used in order to keep liquid waste from staying trapped in the waste disposal line 44 prior to disconnecting the line from the waste container 42.

Figure 3:
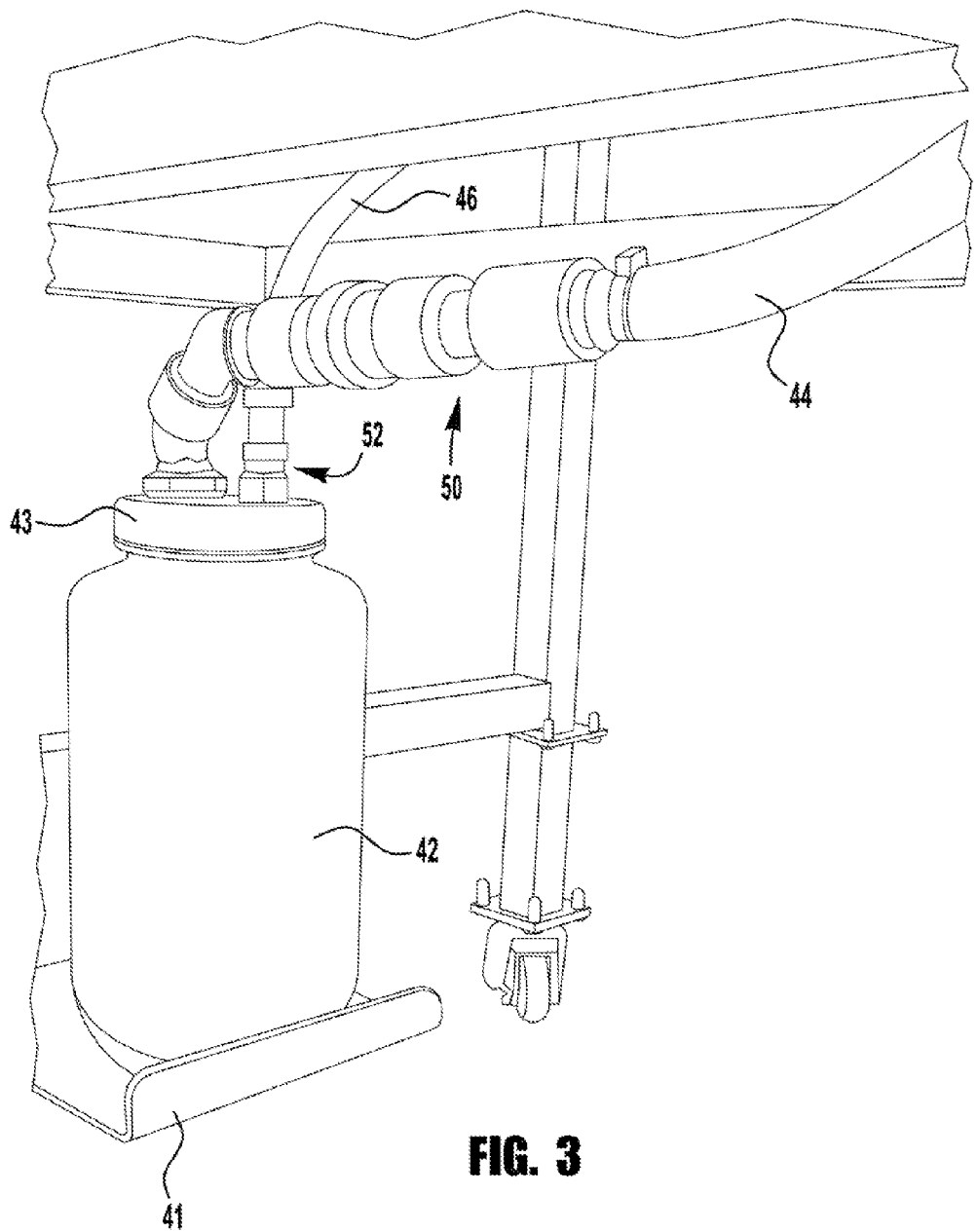
FIG. 3 is a three dimensional view of a waste container with a waste disposal line and an air vent line, each having two double valves, in accordance with the present invention.

FIG. 3 illustrates a detailed three-dimensional view of a waste container 42, which is connected to the waste tank 36, with both a waste disposal line 44 and an air vent line 46. The waste container 42 has a lid 43 into which is attached the waste disposal line 44 and the air vent line 46. The hazardous liquid waste from the waste tank 36 is channeled to the waste container through the disposal line 44. The air that is displaced from the waste container 42, when the hazardous liquid waste enters from the waste tank 36, is channeled through the air vent line 46, the waste tank 36, and the vent line 40 to the exhaust plenum 37 and is ultimately expelled through the exhaust outlet 29, as described above. A typical waste container 42 is a 4-liter container, and is constructed out of material such as HDPE (High Density Polyethylene). Other materials (e.g. glass) may be used dependent on the physical and chemical properties of the waste and waste stream requirements. The waste container 42 is preferably placed in a tray 41 as a secondary containment to collect any liquid which might leak from the container 42.

Figure 4:
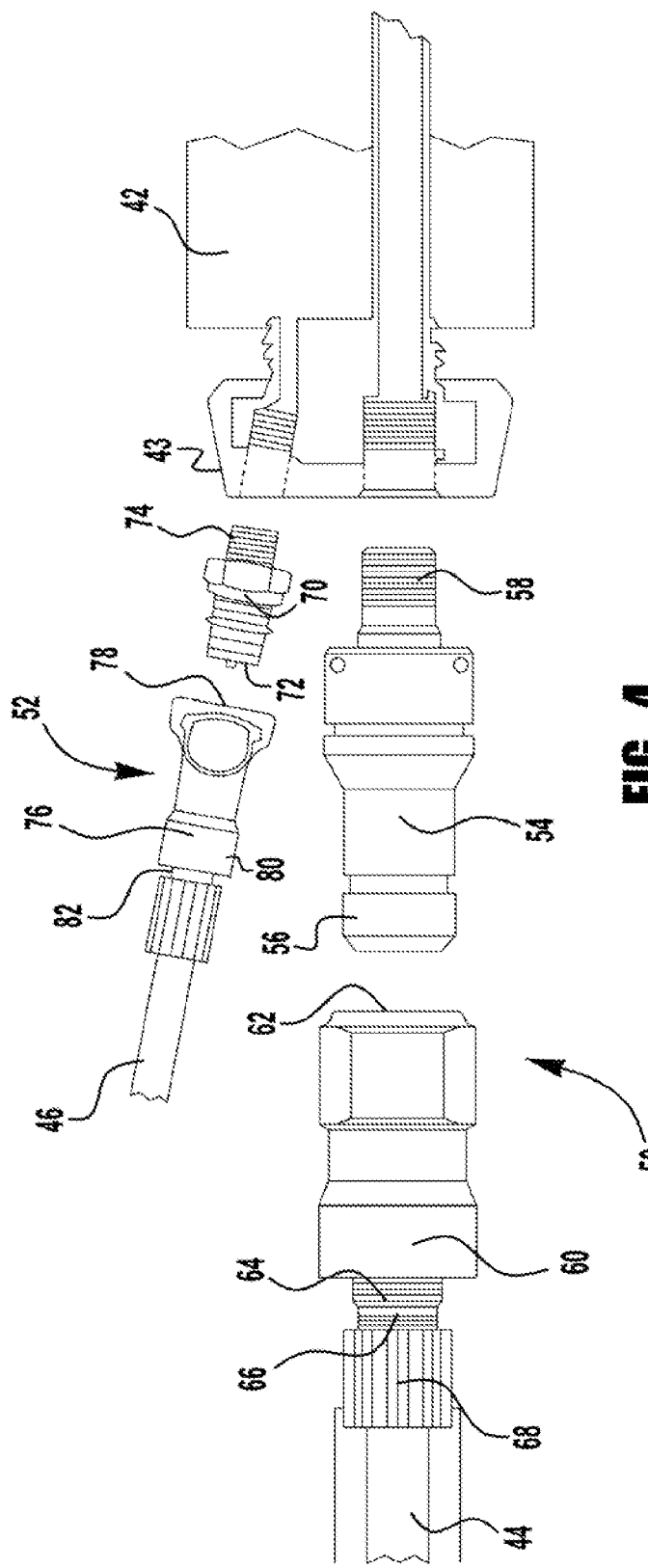
FIG. 4 is a side view of the two double valves for use with a waste disposal line and an air vent line, in accordance with the present invention.

The waste disposal line 44 has a double-valved connector 50 to the lid 43 and the air vent line 46 has a double-valved connector 52 to the lid 43, as seen in FIG. 3. A detailed view of the two double-valved connectors 50 and 52, is seen in FIG. 4. The double valve connectors may be constructed of any type of appropriate valve, for example a ChemQuik liquid line coupling, incorporating biased closed valves in each of the double valve connectors.

As shown in FIG. 4, the double-valved connector 50 includes a liquid line coupling insert 54 including a biased valve (not shown) closing the open end 56. The opposite end 58 of the coupling insert 54 is mounted to the removable lid 43. The double-valved connector 50 also includes a liquid line coupling body 60 having a biased valve (not shown) closing the opened end 62. The opposite end 64 has a threaded hollow extension 66 onto which the flexible 44 disposal line 44 is secured with a threaded fitting 68. In operation, when the liquid line coupling body 60 having the disposal line 44 attached thereto is coupled to the liquid line coupling 54, the biased valves in the liquid line coupling insert 54 and liquid line coupling body 60 are both opened so that liquid waste can flow from the waste tank 36 to the waste container 42. Further, when the liquid line coupling body 60 is uncoupled from the liquid line coupling 54, the biased valves in the liquid line coupling insert 54 and liquid line coupling body 60 are both closed so that both the waste tank 36 and the waste container 42 is completely sealed to the surrounding environment.

Referring again to FIG. 4, the double-valved connector 52 includes a coupling insert 70 including a biased valve closing the open end 72. The opposite end 74 of the coupling insert 70 is mounted to the removable lid 43. The double-valved connector 52 also includes a vent line coupling body 76 having a biased valve (not shown) closing the opened end 78. The opposite end 80 has a threaded hollow extension 82 onto which the flexible air line 46 is secured with a threaded fitting 84. In operation, when the vent line coupling body 76 having the air vent line 46 attached thereto is coupled to the coupling insert 70, the biased valves in the coupling insert 76 and coupling body 70 arc both opened so that air can flow from the waste container 42 to the waste tank 36. Further, when the coupling body 76 is uncoupled from the coupling body 70, the biased valves in the coupling insert 76 and coupling body 70 are both closed so that both the waste tank 36 and the waste container 42 is completely sealed to the surrounding environment.

In sum, when the double-valved connectors 50 and 52 are uncoupled the lines 44 and 46 are closed and the waste tank 36 is closed. The waste contents found in the waste container 42 are likewise sealed from the atmosphere.

In use, after the chemical tests have been completed, the hazardous waste from the glove box 12 is transferred first to the waste tank 36, and then through waste disposal line 44 to waste container 42. Meanwhile, as the waste fills the waste container 42, the displaced air from the waste container flows into the waste tank 36, through air vent line 46, and then through the air vent line 40 to the exhaust plenum 37 and then through the exhaust outlet 29.

The waste disposal line double-valved connector 50 and the vent line double-valved connector 52 allow the waste container 32 to be removed from the glove box 12, while automatically closing the valves, keeping the disposal system 10 in a closed loop. When the double-valved connector 50 and the vent line double-valved connector 52 are disconnected, the waste container 42, with the attached lid 43 having the coupling insert 70 and the coupling insert 54 is placed under a fume hood or any other suitable engineering control, not shown. A fume hood is a type of local ventilation device that is designed to limit exposure to hazardous or noxious fumes, vapors or dusts. A fume hood is typically a large piece of equipment enclosing five sides of a work area, the bottom of which is most commonly located at a standing work height. Once the waste container 42 with the lid is within the fume hood, the lid 43 is removed and replaced for a regular lid. Then, the lid 43 with attached coupling insert 70 and the coupling insert 54 is attached to a fresh waste container 42, and reconnected to the disposal system 10 via the waste disposal line 44 and the air vent line 46, to rccomplete the system.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. A system to safely dispose of hazardous liquid waste, comprising:
   a glove box for conducting a test with a hazardous liquid material therein, the glove box having a drainage line connected to a waste tank for directing the hazardous liquid waste from the glove box to the waste tank;
   a waste disposal line connected at one end to the waste tank and at a second end to a waste container; and
   a double-valved connector connected at one end to the waste disposal line and at the opposite end to the waste container; the double-valved connector including a coupling insert secured at one end to the waste container and having a first biased valve closing the opposite open end thereof, the double-valved connector having a coupling body secured at one end to the waste disposal line and having a second biased valve closing the opposite opened end thereof, and the coupling insert being removably secured to the coupling body whereby when the coupling insert is secured to the coupling body the first and second biased valves are open so that liquid waste can flow from the waste tank to the waste container; and
   when the coupling body is uncoupled from the coupling insert, the first and second biased valves in the coupling insert and the coupling body are biased closed such that both the waste tank and the waste container are completely sealed to the surrounding environment.

2. The system of claim 1, wherein the opposite end of the coupling insert engages the second biased valve in the coupling body to open the second biased valve when the coupling insert is secured to the coupling body.

3. The system of claim 2, wherein the opposite end of the coupling body engages the first biased valve in the coupling insert when the coupling body is secured to the coupling insert.

4. The system of claim 1, wherein the waste container has an air outlet port and the waste tank has an air inlet port with one end of an air vent line secured thereto, a double-valved air connector connected at one end to the air vent line and at the opposite end to the outlet port of the waste container.

5. The system of claim 4, wherein the double-valved air connector includes an air coupling insert secured at one end to the waste container and having a first biased air valve closing the opposite open end thereof, the double-valved air connector having an air coupling body secured at one end to the air vent line and having a second biased air valve closing the opposite opened end thereof, and the air coupling insert being removably secured to the air coupling body whereby when the air coupling insert is secured to the air coupling body the first and second air biased valves are open so that displaced air can flow from the waste container to the waste tank; and
   when the air coupling body is uncoupled from the air coupling insert, the first and second air biased valves in the air coupling insert and the air coupling body are biased closed such that both the waste tank and the waste container are completely sealed to the surrounding environment.

6. The system of claim 5, wherein a removable lid is secured to the waste container, and the double-valved connector and the double-valved air connector are both connected to the removable lid and to the air vent line and waste disposal lines, respectively.

7. The system of claim 6, further including an air vent line between the waste container and an exhaust plenum in the glove box.

8. The system of claim 1, wherein the waste disposal line between the waste container and waste tank is flexible.

9. The system of claim 4, wherein the air vent line between the waste container and waste tank is flexible.

10. The method of safely disposing hazardous liquid waste, comprising:
    conducting a test with a hazardous liquid material in a glove box;
    directing the hazardous liquid waste from the glove box to a waste tank through a drainage line;
    connecting the waste tank to a waste container with a waste disposal line;

connecting the waste disposal line to the waste container with a double-valved connector having a coupling insert connected at one end to the waste container and with a first biased valve closing an opposite end thereof and a coupling body with a second biased valve closing one end and connected at an opposite end the waste disposal line;

and removably securing the coupling insert being to the coupling body whereby when the first and second biased valves are open liquid waste can flow from the waste tank to the waste container; and uncoupling the coupling body from the coupling insert whereby the first and second biased valves are biased closed so that both the waste tank and the waste container are completely sealed to the surrounding environment.

11. The method of claim 10, wherein securing the coupling insert to the coupling body causes second biased valve to open.

12. The method of claim 11, including securing an air vent line between the air outlet port of the waste container and an air inlet port the waste tank, and connecting the air vent line to an outlet port of the waste container with a double-valved air connector.

13. The method of claim 12, including:
providing the double-valved air connector with an air coupling insert secured at one end to the waste container and having a first biased air valve closing the opposite open end thereof;
providing the double-valved air connector with an air coupling body secured at one end to the air vent line and having a second biased air valve closing the opposite open end thereof; and removably securing the air coupling insert to the air coupling body whereby the first and second air biased valves are open so that displaced air can flow from the waste container to the waste tank; and
uncoupling the air coupling body from the air coupling insert whereby the first and second air biased valves are biased closed such that both the waste tank and the waste container are completely sealed to the surrounding environment.

14. The method of claim 12, further including closing the waste container with a removable lid having the double-valved connector and the double-valved air connector connected to the removable lid and to the waste disposal line and the air vent line, respectively.

15. The method of claim 14, including uncoupling the air coupling body from the air coupling insert and uncoupling the coupling body from the coupling insert whereby the waste container and the waste tank are completely sealed to the surrounding environment.

16. The method of claim 15, including transporting the waste container with liquid hazardous waste to a fume hood.

17. The method of claim 16, including removing the removable lid having the double-valved connector and the double-valved air connector connected thereto from the waste container disposed under the hood while the second biased valve and the second biased air valve are closed.

18. The method of claim 17, including mounting the removable lid having the double-valved connector and the double-valved air connector connected thereto to an empty waste container.

19. The method of claim 18, including:
transporting the waste container to a location near the waste tank;
securing the coupling insert being to the coupling body whereby when the first and second biased valves are open liquid waste can flow from the waste tank to the waste container; and
securing the air coupling insert to the air coupling body whereby the first and second air biased valves are open so that displaced air can flow from the waste container to the waste tank.

20. The method of claim 12, including providing an air vent line between the waste container and an exhaust plenum in the glove box.

* * * * *